United States Patent [19]

Cameto et al.

[11] 4,159,803

[45] Jul. 3, 1979

[54] CHAMBER FOR ULTRASONIC AEROSOL GENERATION

[75] Inventors: Leon R. Cameto, Oakland; John R. Edmund, Berkeley, both of Calif.

[73] Assignee: MistO₂Gen Equipment Company, Oakland, Calif.

[21] Appl. No.: 783,105

[22] Filed: Mar. 31, 1977

[51] Int. Cl.² .............................................. B05B 17/06
[52] U.S. Cl. ...................................... 239/102; 239/338
[58] Field of Search ........................ 128/DIG. 2, 194; 239/102, 328, 338; 261/DIG. 48; 229/DIG. 14; 150/1

[56] References Cited

U.S. PATENT DOCUMENTS

| 3,433,461 | 3/1969 | Scarpa | 239/102 X |
| 3,469,785 | 9/1969 | Boucher et al. | 239/102 X |
| 3,774,602 | 11/1973 | Edwards | 128/DIG. 2 |
| 3,989,182 | 11/1976 | Stearley | 229/DIG. 14 |
| 4,071,187 | 1/1978 | Lafleur | 229/DIG. 14 |

Primary Examiner—John J. Love
Attorney, Agent, or Firm—Townsend and Townsend

[57] ABSTRACT

A sanitary chamber is described which operates at room temperature to nebulize or aerosolize a liquid utilized in inhalation therapy. The chamber is a disposable thin walled flexible reservoir for containing a supply of liquid and for dispensing breathable gas such as air in admixture with the liquid. The chamber includes a flexible diaphragm responsive to ultrasonic vibrations of an abutting electroacoustic transducer for admixing the liquid and gas. The chamber further includes integrally formed dispensing means which serves to direct the emanating gas-liquid admixture in an ascending vortex pattern to promote evaporation at ambient temperature. In a particular embodiment, the chamber comprises an inflatable bag constructed of low-cost plastic film material which lends itself readily to compact and sterile storage and disposal.

4 Claims, 4 Drawing Figures

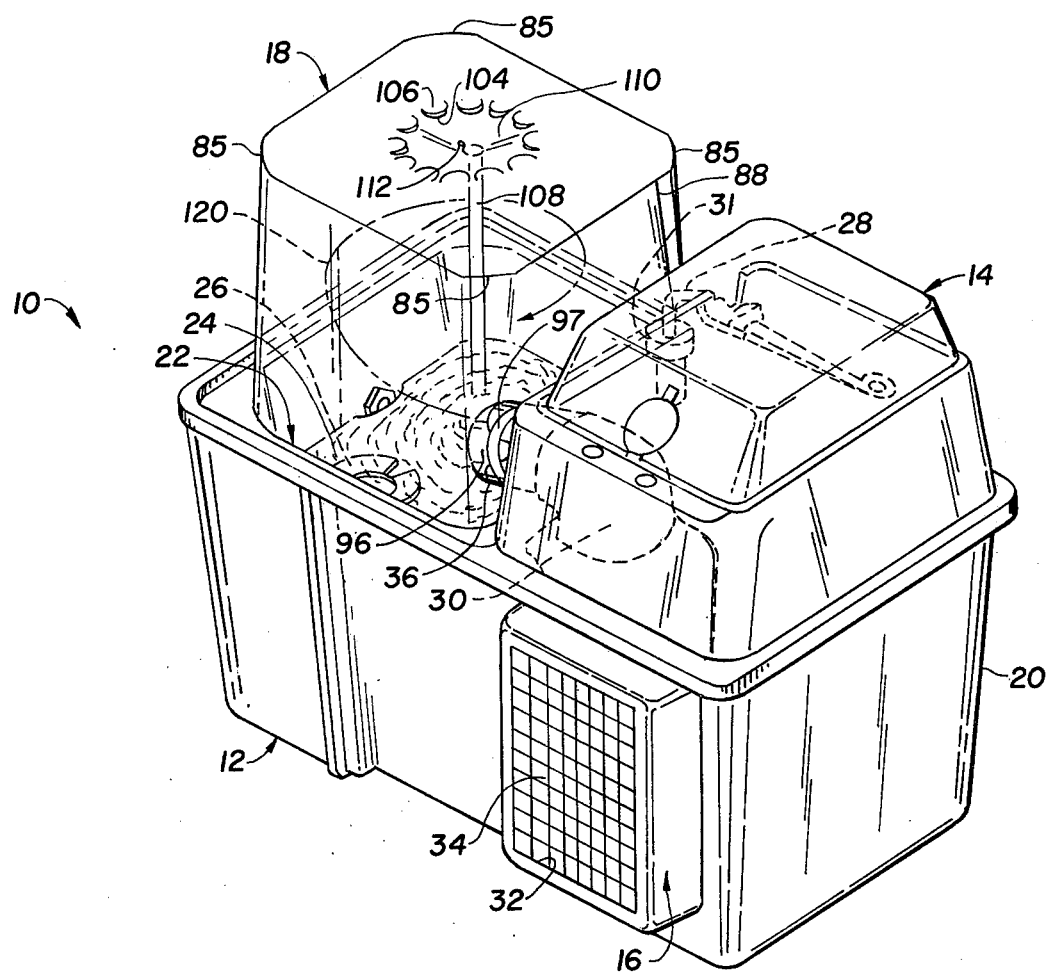
FIG._1.
FIG._2.

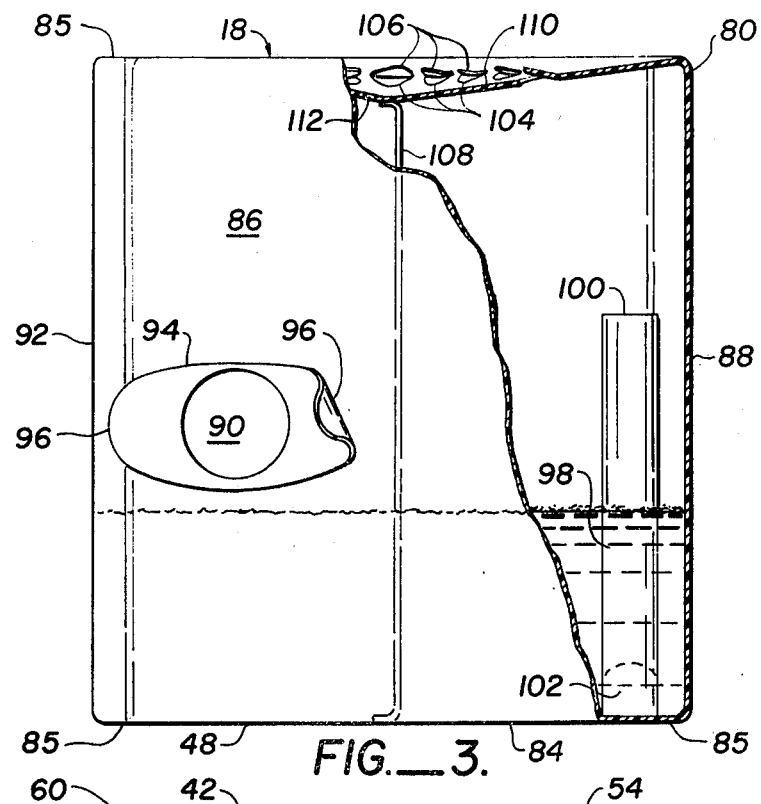
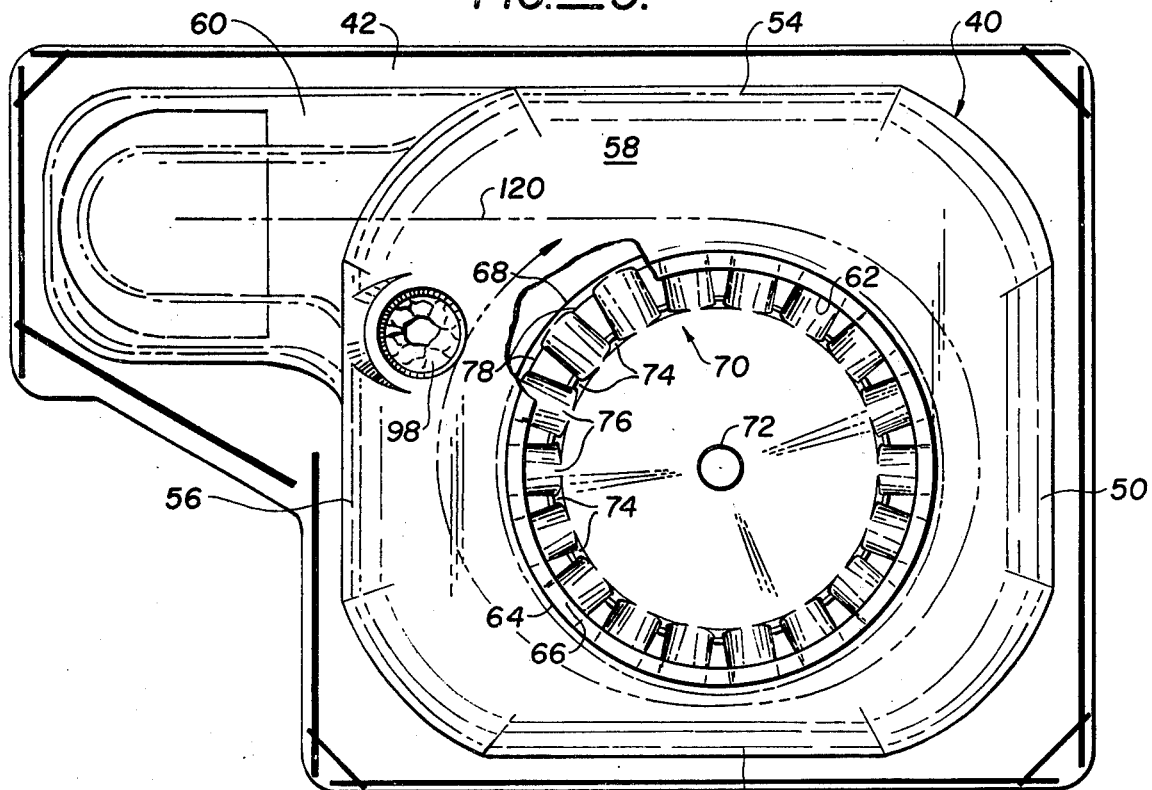

CHAMBER FOR ULTRASONIC AEROSOL GENERATION

BACKGROUND OF THE INVENTION

This invention relates to ultrasonic liquid nebulizing apparatus for atmospheric humidification and more particularly to a chamber for generating an ambient temperature aerosol within a room or the like for use in inhalation therapy.

In the treatment of respiratory diseases, techniques are employed which involve the inhalation by the patient of aerosols. Conditions accompanying many respiratory diseases are respiratory congestion and inadequate expulsion by the patient of secretions from the lungs. It has been found that a water or saline aerosol introduced into the lungs at room temperature assists in relieving and in correcting these conditions. It is conventional practice to directly introduce a medicine, such as a relaxant for treatment of asthma, into the human respiratory system in aerosol form.

Humidifiers, as they are commonly known, are of two general varieties: hot liquid vaporizers and cool vapor aerosol generators. Aerosolizers or nebulizers for cool vapor generation utilized in inhalation therapy have generally included a reusable reservoir provided with a supply of liquid and a supply of breathable gas under substantial pressure. In one type, a liquid discharge nozzle and a gas discharge nozzle are typically arranged so that a stream of the gas is discharged past the liquid to provide a mixture of gas and nebulized liquid for breathing by the patient. In another type, a whirling blade is disposed to dip intermittently into the liquid supply thereby lifting the liquid into the path of a stream of transport gas. These conventional types of nebulizers frequently do not produce aerosol particles of uniformly small character or cause evaporation which would result in deep relaxing penetration of the aerosol into the respiratory system. Nebulizers have recently been developed which utilize ultrasonic acoustic techniques for aerosol generation. See, for example, U.S. Pat. No. 3,861,386.

A major problem associated with cold vapor respiratory therapy is the avoidance of contamination of the generated vapor by impurities carried by the recirculated ambient air. As the air recirculates through the liquid containing chamber, contaminants accumulate which can ultimately cause the transmitttal of a concentration of dangerous infectants. In the past, it has been the practice to frequently sterilize the vapor generator, especially the liquid reservoir, and then provide the liquid supply with a suitable disinfectant. Therefore, relatively frequent, expensive and somewhat cumbersome servicing of the vapor generator is required in order to maintain the requisite high standard of sanitation.

SUMMARY OF THE INVENTION

The above-noted and other disadvantages associated with conventional nebulizers are avoided by use of a nebulizer of the present invention in which the contaminant exposed element of the nebulizer is disposable. In particular, the nebulizer according to the invention comprises a disposable chamber for containing a supply of therapeutic liquid and for dispensing breathable gas such as ambient air in admixture with the liquid. The chamber includes a flexible diaphragm responsive to ultrasonic vibrations of an abutting electroacoustic transducer for admixing the liquid and the gas, and further includes a dispensing means integrally formed in the upper wall of the chamber which serves to direct the emanating gas-liquid admixture in an ascending vortex pattern to promote evaporation at ambient temperature.

In one preferred embodiment, the chamber is a collapsible bag of flexible plastic film which inflates to a desired shape during operation. In particular, the nozzle means of the flexible gas chamber comprises a ring of arcuate slits in a wall of the chamber above the normal liquid level wherein the slits form inwardly facing flaps disposed to direct the fluid admixture toward the center of the ring. Further, the plane of the ring is arranged to be transverse of the normal circulating fluid flow within the chamber. The center of the ring is maintained at a depressed orientation relative to the periphery of the ring by a strap trying opposing sides, i.e., the upper and lower walls, of the flexible bag. A small orifice in the depression provides drainage of accumulated condensate back into the reservoir. This prevents liquid sputtering at the output slits which would otherwise generate undesired discontinuities and non-uniformities in the nebulized output. The depression additionally assures the creation of a horizontal radially inwardly directed component of the nebulized output.

Accordingly, it is one of the purposes of the present invention to provide an apparatus for generating an aerosol from a liquid by means of ultrasonic waves. In particular, this invention provides a sanitary aerosol generator and air scrubber for medical application. The aerosols so generated have a relatively uniform particle size. In addition, the nebulizer inhibits the transmittal of accumulated contamination by providing an inexpensive nebulizing chamber which is disposable.

A particular feature of the nebulizer according to the invention is a novel fluid dispensing nozzle integrally formed in a disposable package. A separate reusable structure is not needed so the requirement of frequent and relatively expensive sterilization procedures is eliminated.

Another purpose of the invention is to provide a sterile nebulizing chamber which is easily stored, transported and discarded. This purpose is achieved by providing a collapsible (i.e., inflatable) chamber made of an inexpensive plastic film material integrally incorporating all requisite fluid inlet and outlet features and acoustic coupling features necessary for providing the desired aerosol output.

In addition to the foregoing purposes, objects and advantages, the invention possesses other advantages set forth in the following description of preferred embodiments of the invention. These features are illustrated in part by the drawings accompanying the specification. It is to be understood, however, that variations in the embodiments may be made without departing from the scope of the invention as set forth in the appended claims.

BRIEF DESCRIPTION OF THE DRAWINGS

In the drawings:

FIG. 1 is a perspective view of one form of the ultrasonic nebulizer embodying the present invention showing the major components thereof and a first preferred embodiment of a nebulizing chamber;

FIG. 2 is a vertical elevational view in partial cross-section illustrating a second preferred embodiment of a nebulizing chamber according to the invention;

FIG. 3 is a side-elevational view in partial cutaway and cross-section illustrating the first preferred embodiment of the nebulizing chamber; and FIG. 4 is a top elevational view in partial cutaway showing the second preferred embodiment of the chamber.

DETAILED DESCRIPTION OF THE PREFERRED EMBODIMENTS

An ultrasonic nebulizer 10 according to the invention comprises four components, an ultrasonic wave generator or oscillator 12, a liquid supply reservoir 14, a gas source inductor 16, and a nebulizing chamber 18. The nebulizer 10 may be secured in a unitary housing 20 having an open-topped basin 22 for partially containing the nebulizing chamber 18. The basin 22 may include a bottom wall 24 in which is mounted an electroacoustic transducer 26, and the liquid supply reservoir 14 may be disposed adjacent and slightly elevated relative to the basin 22 and included a liquid outlet conduit 28 which leads to the basin 22.

The gas source 16 may comprise a fan 30, an inlet opening 32, an air filter 34, and an outlet nozzle 36. The outlet nozzle 36 is preferably disposed to direct a flow of air horizontally along a side of the basin 22 and thus along a side wall of chamber 18.

The ultrasonic oscillator 12 is preferably of the type commonly used for producing tuned, relatively high-power electromagnetic radio frequency energy. The radio frequency output of the oscillator 12 is coupled to the electroacoustic transducer 26, which may be a wafer of piezoelectric ceramic crystal. The crystal transducer 26 is suitably resiliently mounted to permit free vibration when radio frequency energy from the oscillator 12 is impressed thereupon.

Turning now to FIG. 2, there is shown one embodiment of a nebulizing chamber 118 suitable for placement in the basin 22. The chamber 118, which may be of substantially transparent plastic film includes a lower shell 38 and an upper shell 40 joined along a seam 42. The lower shell 38 includes four side panels 44 and a bottom panel 46. The lower shell 38 or merely a portion of bottom panel 46 may be formed of thinner substantially more pliant material than other portions of the chamber 118. The thinner region is preferably offet from the center and intended to be juxtaposed with the crystal transducer 26 as a pliant diaphragm 48. The diaphragm 48, which may have a thickness of up to about 0.005 inch, provides minimal structural support for the lower shell 38 and is adapted to intimately contact the transducer 26 when the chamber 118 is partially filled with liquid. The seam 42 may rest upon the lip of the basin 22 (FIG. 1) to furnish additional structural support.

The upper shell 40 comprises side panels, 50, 52, 54 and 56, top panel 58 and a lateral extension 60. As seen most clearly in FIG. 4, the lateral extension 60 is offset from the center of panel 56. The extension 60 is adapted to mate with an air nozzle 136 (shown in phantom in FIG. 2) of a fan (not shown).

Top panel 58 defines a relatively large central circular opening 62 of relatively large diameter. The circular opening 52 includes a raised flange 64 with a radially inwardly extending lip 66. A removable frustroconical baffle 68 mates with the flange 64 from the inner side of upper shell 40. The rim of the baffle 68 includes a castellation 70 defining a pattern of radially disposed orifices between the raised flange 64 and the baffle 68. The baffle 68 includes a cylindrical projection 72 at the apex of the cone which served as a knob for mounting the baffle 68 to the central opening 62.

Referring to FIG. 4, in conjunction with FIG. 2, the castellation 70 is formed by a plurality of columns 74 extending outwardly from the surface of the baffle 68 defining radially inwardly directed outlets 76 between each adjacent column 74. The nozzle cross-section at the inlet, i.e., the outer radial edge of the baffle 68, is approximately equal to the nozzle cross-section at the outlet, i.e., facing the projection 72, and the length of the nozzle is approximately equal to the minimum width. Thus, in conjunction with the radially inwardly extending lip 66 which forms the top of the outlet 76, the inlet portion has a relatively deep U-shape and the outlet portion has a relatively shallower U-shape. In order to prevent the accumulation of moisture and condensate in the nozzle outlet area on the surface of the baffle 68, the trough of the outlets 76 are below the level of the surface of the insert so they also serve as drainage means for accumulated moisture on the surface of the baffle 68. Thus, runoff can be in virtually any direction into the nebulizing chamber 18 if the housing 20 is substantially level. To aid in alignment of the baffle 68 within the central opening 62, each of the columns 74 is provided with a shoulder 78 which mates with the raised flange 64 and radially extended lip 66.

In operation, the chamber 118 filled with liquid to a desired level receives air through the extension 60, which directs flow in a generally horizontal circulating pattern. An ultrasonic frequency is impressed upon the transducer 26 which vibrates the diaphragm 48 causing cavitation in the adjacent liquid. Bubbles stream to the surface which transforms to a mist at the liquid gas interface. The gas flow conveys the mist to the outlet area. Upon encountering the flange 64 and lip 66, the flow is directed horizontally inwardly in a corkscrew pattern over the external surface of the baffle 68. The exhaust flow defines vortex ascending from the apex of baffle 68 which enhances the evaporation of the mist. In particular, the ascending, swirling mist substantially evaporates upon contact with air to produce the desired humidification of the ambient atmosphere.

Turning now to FIG. 3, another embodiment of the nebulizing chamber 18 is illustrated. The view of FIG. 3 shows the chamber 18 shown in FIG. 1 in a side elevation.

The chamber 18 comprises a collapsible, i.e., inflatable bag 80, of relatively thin pliant material substantially impervious to liquid penetration. The bag 80 has an upper panel 82, a lower panel 84, and a side panel 86. The side panel 86 comprises a rectangular sheet joined on a seam 88 at opposing ends to form a tube. The upper and lower panels 82, 84 may be approximately octagonal, or more precisely, square-shaped sheets with truncated corners 85 and joined along the margins of the sheets to the side panel 86. The upper panel 82 encloses one end of the tube and the lower panel 84 encloses the opposing tube end. The lower portion of the bag 80 generally conforms to the shape of the basin 22 upon inflation.

The bag 80 may be a pliant plastic film material generally impervious to water. Suitable materials are polyethylene, nylon, cellophane, polyvinyl chloride, or Mylar (a DuPont trademark). A wide range of wall thicknesses is satisfactory for the side panel and the top panel. For example, a nominal wall thickness of 0.006 in. to 0.020 in. provides adequate strength and durability. The membrane and lower panel 84, which confronts the transducer 26 and serves as a flexible diaphragm, is preferably as thin as possible in order to prevent undue loss of useful energy to flexure-induced heating. A practical upper limit or membrane is about 0.005 in. The preferred membrane thickness is on the order of 0.001 in. or even less. The membrane thickness is limited only by the availability of ultra-thin material generally impervious to liquid.

Within the side panel 84 of the bag 80 are two openings. The first opening is generally circular orifice 90 which leads directly into the interior of the bag 80. The orifice 90 may be spaced about half way above the bag lower margin and is preferably located near a vertical edge 92 between corresponding truncated corners 85. A collar 94 circumscribes the orifice 90 and includes external flaps 96. The orifice 90 is provided as an inlet for pressurized gas, such as air, which is adapted to mate with the nozzle 36 of a gas supply, such as a fan 30 (FIG. 1). The collar 94 permits the nozzle 36 to be tied by a strap 97 or otherwise secured by the flaps 96 to the nozzle in a manner minimizing gas leakage.

The orifice 90 is located near the edge 92 so that the gas inlet 90 is offset to produce a horizontally circulating gas flow pattern within the bag 80. The bag 80 may also have a circular cylindrical cross-section. In such case, the nozzle 36 of the gas supply is mounted at an offset angle through the side panel 86, and the inlet orifice 90 may be elliptical in shape or otherwise shaped to accommodate and angularly mated gas nozzle 36.

The second side panel opening is a vertical tube 98 which serves as a liquid supply inlet and which may be formed by an overlaid strip bonded to the side panel 86. The tube 98 has an external end 100 located above the bottom of the bag 80 and an internal end 102 opening into the bag and located adjacent the bag bottom. The liquid outlet conduit 28 (FIG. 1) is adapted to be inserted into the tube 98. A ring seal 31 around the outlet conduit 28 provides a substantially airtight contact between the tube 98 and the conduit 28.

The outlet of the nebulizing chamber is located in the upper panel 82. A plurality of slits 104 is cut in the upper panel 82 to define protruding flaps or tongues 106. The slits 104 may be arcuate, and the tongues 106 are preferably arranged in an inwardly facing ring so that they form a radially inwardly facing pattern of aerosol outlet openings.

Between the center of the upper panel 82 and the lower panel 84 is a retaining strap 108 which controls the height of vertical inflation of the bag 80. The length of the strap 108 is shorter than the height of the bag side panel 86 so that a central depression 110 is established within the ring of outlet openings in the upper panel 82 upon full inflation of the bag 80. This depression assures a radially inwardly directed exhaust through the outlet openings. A small drain hole 112 is located near the center of the depression 110 so that any moisture which may collect at the exit of the slits 104 drains from the depression 110. This arrangement assures that moisture does not interfere with the aerosol flow through the slits 104.

The operation of the nebulizer 10 according to the invention may be visualized with reference to FIG. 1. The bag 80 is filled through tube 98 with a liquid to be nebulized from reservoir 14 to a preselected level below the height of the gas orifice 96. The fluid level may be maintained relatively constant by a level sensitive valving arrangement (not shown). As an alternative to filling the bag through tube 98, the bag may be pre-filled with a measured amount of liquid to be nebulized. The liquid to be nebulized may be water, water containing a suitable disinfectant or some other suitable medication in liquid form.

The electroacoustic transducer 26 is excited at ultrasonic frequency by an electrical signal from the oscillator 12. The transducer wafer 26 oscillates axially of its face while it is held in intimate contact with the lower panel 84 by the weight of the liquid within the bag 80. The oscillating crystal induces waves in the liquid which are transmitted through the liquid to the surface to cause the surface to undulate. In addition, a pressure drop occurs in the liquid near the face of the oscillating transducer 26 which causes formation and collapse of cavities or bubbles at an extremely high rate. The bubbles stream toward the surface of the liquid where, upon encountering the interface of the gas and the liquid, a fine mist or aerosol is generated.

Gas, i.e., filtered air from the fan, 30, is supplied through the gas orifice 90 and directed in a generally horizontal circulating pattern 120 over the surface of the liquid. The force of the gas creates a circulating pattern which captures liberated aerosol and conveys it to the outlet openings 104 in the upper panel 82. The aerosol is expelled through the slits 104, which cause the tongues 106 to lift. A back pressure at the outlet openings maintains the bag 80 in an inflated condition. Additionally, the location of the slits 104 in an inwardly facing ring near the center of the nebulizing chamber, in conjunction with a gas circulating pattern having a substantial converging horizontal component, further enhances the mist generation efficiency of the nebulizer by releasing the mist to the atmosphere in an ascending corkscrew pattern which promotes evaporation of the mist upon mixture with the ambient air. The nebulizer may generate as much as 600 to 800 ml per hour at optimum operating efficiency and optimum liquid level. However, as the liquid drops below the optimum level, the efficiency of the nebulizer decreases markedly. Since a period of several hours is required to exhaust all liquid by nebulization after the liquid surface drops below the optimum level, changes in the output of the apparatus will be apparent long before the liquid is exhausted. Thus, the apparatus can be serviced long before damage is done to the apparatus through overheating or the like.

The optimum liquid level approximately corresponds to a multiple of the half wave length of the excitation frequency in the liquid medium. A liquid level of about 3 cm within a chamber about 25 cm in height is satisfactory where the excitation frequency is about 1.4MHz.

Attention to the size and number of slits assures that adequate back pressure is maintained for inflation of the bag at the volume flow rates of interest. For example, for an air volume throughput of 25 to 100 CFM, a satisfactory outlet arrangement is approximately twelve slits, arranged in a circular ring of about four inches in diameter, each slit being a full semicircle of about 7/16 in. radius.

In order to maintain reasonable air purity at high throughput rates, a HEPA (High Efficiency Particulate Air) type filter may be employed at the air intake.

Various means may be employed to provide transport gas. For example, a fan, gas from an external compressor, gas from the plenum of an air conditioner or furnace, or gas from a pressurized tank may be supplied to the nebulizing chamber.

A fan system is perhaps most practical and convenient especially in enclosed rooms. Where room air is recirculated, the device including an air filter may serve as an air scrubber to remove contaminants such as smoke from the atmosphere.

Having illustrated the invention with reference to specific embodiments, other embodiments will be apparent to those of ordinary skill in the art. The invention should therefore be limited only as indicated by the appended claims. For example, the nebulizing may be supplied with a premeasured quantity of liquid to be nebulized so that an external replenishing source would be unnecessary. Thus, upon exhaustion of the liquid supply, the chamber could be discarded.

We claim:

1. A nebulizing chamber for use with an ultrasonic electroacoustic transducer adapted to interface with said chamber, said chamber comprising:
   a thin-walled inflatable bag adapted to enclose a liquid and having outlet means comprising a plurality of slits forming flaps in the upper, normally horizontally disposed chamber wall, wherein said slits are arranged in a ring with the arcuate flaps disposed to direct said exhaust radially inwardly so as to generate an ascending convergent outlet flow pattern wherein said chamber includes a retaining means maintaining a depression within said ring upon inflation of said chamber for directing a portion of said exhaust in a convergent, substantially horizontal direction.

2. A nebulizing chamber for use with an ultrasonic electroacoustic transducer adapted to abut said chamber, said chamber comprising:
   an inflatable bag of thin plastic film having top and bottom walls, side walls, a liquid inlet passage, and a gas inlet passage, said gas inlet passage being in a side wall and and disposed to permit introduction of transport gas in a generally horizontally circulating flow pattern;
   outlet means in the top wall for dispensing a gas/liquid aerosol mixture, said outlet means comprising a plurality of arcuate slits arranged in a ring so as to form a plurality of radially inwardly disposed openings with inwardly directed flaps;
   a strap tying the bottom wall to the top wall at a location within the ring to form a depression in the ring upon bag inflation for maintaining a radially inwardly directed outlet flow component to promote an ascending vortex pattern of aerosol; and
   a hole within the depression for draining accumulated moisture.

3. A nebulizing chamber adapted to abut an electroacoustic transducer within an enclosing cavity, said chamber comprising:
   a collapsible bag having all walls constructed of a thin, flexible plastic film material, said bag being adapted to inflate to a desired shape at least partially defined by said enclosing cavity only upon induction of pressurized gas into said bag and further being adapted to enclose a supply of liquid, a wall of said bag adapted to abut an ultrasonic transducer;
   outlet nozzle means integrally formed in a wall of said bag above the normal liquid level of said bag, said nozzle means comprising perforations in said film material of a size sufficiently small to provide a back pressure to assure inflation, wherein said perforations of said outlet nozzle means comprise arcuate slits arranged in a ring in said top wall, said slits defining arcuate flaps disposed to direct exhaust from said nozzle means in a convergent direction.

4. A nebulizing chamber according to claim 3 further including means disposed within said ring for returning condensate to the interior of said bag.

* * * * *